United States Patent [19]

Hardt

[11] Patent Number: 4,703,126
[45] Date of Patent: Oct. 27, 1987

[54] PROCESS FOR THE PRODUCTION OF 7-ETHYL INDOLE

[75] Inventor: Peter Hardt, Visp, Switzerland

[73] Assignee: Lonza Ltd., Gampel/Valais, Switzerland

[21] Appl. No.: 896,109

[22] Filed: Aug. 13, 1986

Related U.S. Application Data

[63] Continuation-in-part of Ser. No. 587,593, Mar. 8, 1984, abandoned.

[30] Foreign Application Priority Data

Mar. 23, 1983 [CH] Switzerland .......................... 1584/83

[51] Int. Cl.$^4$ ........................................... C07D 209/08
[52] U.S. Cl. ..................................................... 548/508
[58] Field of Search ............................................ 548/508

[56] References Cited

U.S. PATENT DOCUMENTS

| | | | |
|---|---|---|---|
| 2,891,965 | 6/1959 | Voltz | 260/319 |
| 2,953,575 | 9/1960 | Erner et al. | 548/508 |
| 3,206,471 | 9/1965 | Allen et al. | 260/319 |
| 3,441,569 | 4/1969 | Hargis | 260/319.1 |
| 3,824,252 | 7/1974 | Mauri et al. | 548/508 |
| 3,894,042 | 7/1975 | Tanaka et al. | 260/319 |
| 3,984,434 | 10/1976 | O'Murchu | 548/508 |
| 4,443,615 | 4/1984 | Matsuoka et al. | 548/508 |

FOREIGN PATENT DOCUMENTS

| | | | |
|---|---|---|---|
| 1149395 | 7/1983 | Canada | 548/508 |
| 2148961 | 9/1970 | Fed. Rep. of Germany . | |
| 2049752 | 8/1971 | Fed. Rep. of Germany . | |
| 2224556 | 1/1974 | Fed. Rep. of Germany . | |
| 2257579 | 8/1975 | France . | |
| 589054 | 4/1977 | Switzerland . | |

OTHER PUBLICATIONS

J. Med. Chem., (1980), 23, No. 11, p. 1224, Glennon et al.
Drugs of The Future, vol. II, No. 1, (1977), p. 21.
Tamara, "Indole", Chem. Abst., 89:43110r (1978).
Hegedus et al., "Palladium–Assisted Synthesis of Nitrogen Heterocycles", Chem. Abst., 80:215165f, (1978).
Piozzi et al., Chem. Abst., 60:9231e (1964).
Gipstein et al., Chem. Abst. 71:3755b (1969).
C. Noller, Textbook of Organic Chemistry, p. 81 (1966), W. B. Saunders Co., Philadelphia.
C. Demerson et al., J. Med. Chem. (1976), vol. 19, No. 3, p. 391.
G. Hawley, Condensed Chemical Dictionary, pp. 205–206, Von Nostrand Reinhold Co., N.Y. QD5C5 (1981).

Primary Examiner—Mary E. Ceperley
Attorney, Agent, or Firm—Fisher, Christen & Sabol

[57] ABSTRACT

Process for the production of 7-ethyl indole by dehydrocyclization of 2,6-diethylaniline and then partial hydrogenation of the accumulated raw product.

8 Claims, No Drawings

PROCESS FOR THE PRODUCTION OF 7-ETHYL INDOLE

This is a continuation-in-part of application Ser. No. 587,593, filed on Mar. 8, 1984, now abandoned.

BACKGROUND OF THE INVENTION

1. Field of the Invention

The invention relates to the production of 7-ehtyl indoles.

2. Prior Art

Indole has been produced from 2-ethylaniline with the help of dehydrogenation catalysts at an elevated temperature between 500° and 700° C.

According to German OS No. 2,049,752 and German OS No. 2,148,961, 2-ethylaniline is converted into indole in the presence of (i) water and oxygen or (ii) an oxygen-containing gas. It was later shown that a corresponding dehydrocyclization in a simplified process can be carried out without the use of oxygen or an oxygen-containing gas with better space-time-yields (Swiss Pat. No. 589,054).

7-Alkyl indoles are accessible as a result of the catalytic dehydrocyclization of the corresponding 2,6-dialkylanilines, but, contrary to indole itself, only with a low selectivity. Thus, 7-ethyl indole has only been obtained from 2,6-diethylaniline with a 40 percent selectivity (U.S. Pat. No. 3,441,569). Other production methods for 7-alkyl indoles are technically expensive or have a low selectivity. Thus, 7-ethyl indole can be obtained from 2-ethylaniline with the help of AlCl$_3$ but with only a 20 percent yield [*J. Med. Chem.*, (1980), 23, No. 11, p. 1224].

In the case of the catalytic dehydrocyclization of 2,6-diethylaniline in the presence of water (Swiss Pat. No. 589,054), a mixture of quite varied compounds is obtained. The 7-ethyl indole contained therein as the main component cannot be obtained easily by distallation since the by-products containing vinyl groups are inclined to spontaneous polymerization reactions. As a result of that fact, technical problems arise and there are high losses of substance and quality.

It is known from U.S. Pat. No. 3,894,042 that 7-ethyl indole can be produced by the catalytic conversion of 2,6-diethylaniline in the presence of steam with the exclusion of oxygen in a per-pass yield of a modest 13.2 mol percent.

BROAD DESCRIPTION OF THE INVENTION

The main object of the invention is to provide a process for the production of 7-ethyl indole which avoids the disadvantages of the known processes. Other objects and advantages are set out herein or are obvious herefrom to one skilled in the art.

The objects and advantages of the invention are achieved by the process of the invention.

The invention involves a process for the production of 7-ethyl indole by the catalytic dehydrocyclization of 2,6-diethylaniline. The 2,6-diethylaniline is dehydrocyclized, without the addition of oxygen or an oxygen-containing gas, in the presence of steam and a copper chromite catalyst.

The catalyst has been activated with barium oxide at a temperature between 500° and 700° C. and at a pressure between 0.013 and 10 bar. The molar ratio of the steam to the starting material is within the range of 3 to 1 to 75 to 1. The raw product obtained by the dehydrocyclization is subjected in a further step to a partial hydrogenation by means of a hydrogenating catalyst to obtain the desired 7-ethyl indole.

Preferably the catalytic partial hydrogenation is carried out at a temperature of 40° to 120° C. Also, preferably the partial hydrogenation is carried out under a H$_2$ pressure of 4 to 12 bar. Preferably Raney nickel or a precious metal is used as the hydrogenation catalyst.

DETAILED DESCRIPTION OF THE INVENTION

The dehydrocyclization catalyst can be used in a solid bed as well as in a moving bed or a fluid bed. The dehydrocyclization catalyst essentially does not lose its effectiveness after long periods of usage and its activity is completely preserved. Therefore, reactivation of the catalyst is not necessary.

Additionally, an inert diluent can be used which can be nitrogen, argon, carbon dioxide, a saturated hydrocarbon, such as, n-pentane, isopentane, n-hexane and n-heptane, or any other substance which will not be changed under the conditions of reaction. The molar ratio of steam to the aromatic starting product can be varied within the range of 3:1 to 75:1.

The dehydrocyclization is carried out at a temperature of 500° to 700° C., preferably at 550° to 650° C. The reaction pressure can be varied within the broad range of 0.013 to 10 bar, but the process preferably is carried out at atmospheric pressure.

The apparent contact time between the reaction participants and the catalyst lies within the range of 0.1 to 60 seconds, with the range of 0.5 to 30 seconds being particularly preferred. The phrase "apparent contact time between the reaction participants and the catalysts" is to be understood to be the ratio between the volume of the catalyst bed and the flow of the reaction participants as the gas under the reaction conditions.

It has been found that, by means of a partial hydrogenation carried out following the catalytic dehydrocyclization, the vinyl groups present in the reaction mixture are hydrogenated to the corresponding ethyl groups.

Partial hydrogenation of the raw product (obtained from the dehydrocyclization of the 2,6-dialkylaniline) is conducted in an autoclave with stirring with the use of Raney nickel as a hydrogenation catalyst or a nickel, palladium, platinum or ruthenium catalyst (i.e., a precious metal catalyst) which is used in a quantity of 0.1 to 1 percent, preferably 0.3 to 0.6 percent.

The hydrogenation is preferably carried out at a temperature of 40° to 120° C., most preferably at 50° to 60° C. The pressure applied during the hydrogenation is preferably 4 to 12 bar, but most preferably a H$_2$ pressure of 5 to 6 bar is used.

As a result, the composition of the reaction mixture is simplified by the partial hydrogenation step, and accordingly the percentage share of 7-ethyl indole in the reaction mixture is increased. The 7-ethyl indole in a high degree of purity can be isolated from the reaction mixture without technical problems.

7-ethyl indole is an important intermediate product for the production of pharmaceutical agents. [*J. Med. Chem.*, (1976), Vol. 19, No. 3, p. 391, and *Drugs of the Future*, Vol. II, No. 1, (1977), p. 21]. The 7-ethyl indole is prepared by the simple and efficient process of the invention in a good yield and with high purity. Thus, as a result of the production process of the invention, there is conversion of up to 78 percent of the 2,6-diethylaniline, and 7-ethyl indole with a selectivity of 67 percent is obtained.

By way of summary, the invention involves a process for the production of 7-ethyl indole through the dehydrocyclization of 2,6-diethylaniline and the subsequent partial hydrogenation of the raw (intermediate) product obtained.

As used herein, all percentages, parts, ratios and proportions are on a weight basis unless otherwise stated herein or obvious herefrom to one ordinarily skilled in the art. Also as used herein, the conversion relates to the educt used, and the selectivity is the yield and is related to the converted educt.

EXAMPLE 1

7-Ethyl indole

The reactor for the dehydrocyclization contained 0.5 liter of Cu-chromite/BaO catalyst in table form (4×4 mm). The reactor was heated to 660° C. and was fed 68 g of 2,6-diethylaniline and 81 g of water per hour. After cooling, a mixture of a heavily organic phase and of a lighter water phase, as well as a waste (discharge) gas, was obtained in the recipient vessel. The waste gas had the following typical composition (vol. percent): 80.0 percent of hydrogen; 2.9 percent of methane; 2.0 percent of ethane; 0.4 percent of ethylene; 2.0 percent of carbon monoxide; and 10.7 percent of carbon dioxide. Obtained per hour were 38 l of waste gas, 59 g of organic raw product and 76 g of water which can be used again. The organic raw product had the following composition:

| | |
|---|---|
| 2-ethylaniline | 2.4 percent |
| 2-methyl-6-ethylaniline | 2.2 percent |
| 2,6-diethylaniline | 22.4 percent |
| 2-ethyl-6-vinylaniline | 6.4 percent |
| indole | 1.8 percent |
| 7-methyl indole | 3.9 percent |
| 7-ethyl indole | 46.5 percent |
| 7-vinyl indole | 11.5 percent |

A converson of 80.6 percent and a selectivity of 51.4 percent correspond to these results.

295 g of the raw product was hydrogenated in a stirring autoclave after the addition of 1.2 g of Raney nickel at 55° C. and a pressure of 5 bar of $H_2$ until saturation. After cooling the autoclave to 20° C., expansion, and filtering of the catalyst, 290.5 g of a liquid having the following composition was obtained.

| | |
|---|---|
| 2-ethyl aniline | 2.6 percent |
| 2-methyl-6-ethyl aniline | 2.5 percent |
| 2,6-diethyl aniline | 29.1 percent |
| indole | 1.8 percent |
| 7-methyl indole | 3.8 percent |
| 7-ethyl indole | 58.2 percent |

A conversion of 75.1 percent and a selectivity of 68.0 percent obtained by the two steps, namely, dehydrocyclization and partial hydrogenation, correspond to these results.

EXAMPLE 2

7-Ethyl indole

The reactor filed with Cu-chromite/BaO catalyst was heated to 610° C. Into the reactor was fed 68.4 g of 2.6-diethylaniline and 41.4 g of water per hour. The organic reaction product after 5 hours of such reaction conditions was collected and subjected to partial hydrogenation as described in Example 1. After filtering of the hydrogenation catalyst, 332.4 g of organic liquid containing 45.8 g percent of 2.6-diethylaniline and 41.0 percent of 7-ethyl indole was obtained.

EXAMPLE 3

7-Ethyl indole

Into the reactor containing 0.5 l of Cu-chromite/BaO catalyst, which had already been used a total of 200 hours, and heated to 650° C., was fed 71.7 g of 2,6-diethylaniline and 79 g of water per hour. Over a period of 8 hours, 521.8 g of organic phase was obtained. Then, after addition of 0.8 g of Raney nickel, which contained 10 percent Co, it was hydrogenated in an autoclave with stirring at 55° C. and 10 bar of hydrogen until saturation was reached. After cooling and expansion, and filtering of the catalyst, 511.3 g of an organic liquid with the following composition was obtained:

| | |
|---|---|
| 2-ethylaniline | 3.0 percent |
| 2-methyl-6-ethylaniline | 2.4 percent |
| indole | 2.0 percent |
| 2,6-diethylaniline | 29.3 percent |
| 7-methyl indole | 3.5 percent |
| 7-ethyl indole | 57.9 percent |

By fractional vacuum distillation, after a first run, a fraction with 2,6-diethylaniline and an intermediate cut at 140° C./10 mbar of 267.5 g of 98.3 percent 7-ethyl indole were obtained. This result corresponded to a 77.7 percent conversion and a 66.8 percent selectivity.

EXAMPLE 4

7-Ethyl indole 442.5 g of organic raw product, which was produced according to Example 1 and contained:

| | |
|---|---|
| 2,6-diethylaniline | 22.6 percent |
| 2-ethyl-6-vinylaniline | 7.2 percent |
| 7-ethyl indole | 44.2 percent |
| 7-vinyl indole | 12.9 percent | was saturated with hydrogen in an autoclave with stirring after the addition of 2.5 g of platinum catalyst (5 percent on activated carbon) at 55° C. and 6 bar. About 4 hours were required for this purpose. Then the autoclave was cooled, followed expansion. After separation of the catalyst by decanting and centrifuging, 440.4 g of reaction product was obtained, which contained 29.5 percent of 2,6-diethylaniline and 57.1 percent of 7-ethyl indole.

EXAMPLE 5

7-Ethyl indole

Analogously to Example 4, 442.5 g of organic raw product was hydrogenated with 1.5 g of palladium catalyst (5 percent on activated carbon). The reaction was terminated after 6 hours. 438.0 g of reaction product was obtained, in which no compounds containing vinyl groups were any longer detectable.

EXAMPLE 6

7-Ethyl indole

Analogously to Example, 4, 442.5 g of raw product was hydrogenated with 2.5 ruthenium catalyst (5 percent on activated carbon) at 55° C. and 10 bar of hydrogen pressure. No compounds containing vinyl groups could any longer be detected in the reaction product.

EXAMPLE 7

7-Ethyl indole

Analogously to Example 4, 426 g of raw product was hydrogenated with 1.1 g of nickel catalyst for 8 hours at 55° C. and 10 bar. No 2-ethyl-6-vinylaniline was contained in the reaction product and the 7-vinyl indole content had dropped from 12.9 percent to 0.4 percent.

What is claimed is:

1. Process for the production of 7-ethyl indole by the catalytic dehydrocyclization of 2,6-diethylaniline in the presence of steam without the addition of oxygen or an oxygen-containing gas in the presence of a catalyst, characterized in that the dehydrocyclization takes place in the presence of a copper chromite catalyst, which is activated with barium oxide, at a temperature between 500° and 700° C. and at a pressure between 0.013 and 10 bar, the molar ratio of steam to the [7-ethyl indole] 2,6-diethylaniline being within the range of 3 to 1 to 75 to 1, a raw product being obtained which includes 7-ethyl indole and at least one by-product containing a vinyl group, and the resultant raw product, in a further step, is subjected to a partial hydrogenation by means of a hydrogenation catalyst whereby most of the by-product containing a vinyl group is converted to 7-ethyl indole.

2. Process according to claim 1 wherein the catalytic partial hydrogenation is performed at temperature of 40° to 120° C.

3. Process according to claim 2 wherein the partial hydrogenation is performed under an $H_2$ pressure of 4 to 12 bar.

4. Process according to claim 3 wherein Raney nickel is used as the hydrogenation catalyst.

5. Process according to claim 3 wherein a precious metal is used as the hydrogenation catalyst.

6. Process according to claim 1 wherein the partial hydrogenation is performed under an $H_2$ pressure of 4 to 12 bar.

7. Process according to claim 1 wherein Raney nickel is used as the hydrogenation catalyst.

8. Process according to claim 1 wherein a precious metal is used as the hydrogenation catalyst.

* * * * *